United States Patent [19]

Klainer

[11] Patent Number: 4,846,548
[45] Date of Patent: Jul. 11, 1989

[54] FIBER OPTIC WHICH IS AN INHERENT CHEMICAL SENSOR

[75] Inventor: Stanley M. Klainer, San Ramon, Calif.

[73] Assignee: ST&E, Inc., Pleasanton, Calif.

[21] Appl. No.: 46,986

[22] Filed: May 6, 1987

[51] Int. Cl.$^4$ .............................................. G02B 6/02
[52] U.S. Cl. .............................. 350/96.29; 350/96.33; 350/96.34
[58] Field of Search ................. 350/96.29, 96.3, 96.31, 350/96.32, 96.33, 96.34

[56] References Cited

FOREIGN PATENT DOCUMENTS 57-106838  7/1982  Japan .................................. 350/96.29
60-166837  8/1985  Japan .................................. 350/96.29

Primary Examiner—John D. Lee
Assistant Examiner—John Ngo
Attorney, Agent, or Firm—Henry P. Sartorio

[57] ABSTRACT

A fiber optic element is used to detect the presence of chemical or biological species by measuring changes in the total internal reflection characteristics of the element produced by changes in the index of refraction of a clad or layer of a material which reacts with the chemical or biological species.

34 Claims, 2 Drawing Sheets

FIBER OPTIC WHICH IS AN INHERENT CHEMICAL SENSOR

BACKGROUND OF THE INVENTION

The invention relates generally to optical analytical measurements of chemical species and more particularly to fiber optic chemical sensors.

Research and development of sensors for the detection and quantification of particular chemical species or classes of chemical compounds is a fast growing technical field. Yet for all the effort being expended, the development is very much fragmented. Each physical and chemical property to be measured becomes an independent special project because there is no common ground which forms a basic foundation for sensor design. A variety of different types of sensors have been tried, including fiber optic chemical sensors (FOCS), CHEM-FETs, piezoelectric crystals, and semi-conductors. Each sensor requires a different chemistry (or chemical composition) and different sensor design for each specific measurement to be made. Thus each new target material initiates a new research and development effort. Accordingly it is highly desired to provide a basic approach to sensor design which can be utilized for a wide variety of applications by the adoption of a single principle.

Typical fiber optic sensors are illustrated by U.S. Pat. Nos. 4,492,121 to Lehto and 4,542,987 to Hirschfeld in which a fluorescent material is attached to the end of a fiber through which an excitation signal and the resulting response signal are transmitted. U.S. Pat. No. 4,523,092 to Nelson illustrates a similar arrangement in which a series of different absorber materials are mounted to the end of a fiber.

U.S. Pat. No. 4,592,664 to Bijlenga shows a device having a luminescent material at the end of a fiber, including an embodiment in which the luminescent sensor material is the core of a light guide. U.S. Pat. No. 4,040,749 to David shows a waveguide having a liquid crystal material on its surface which is sensitive to organic vapor to change the light transmitting capability of the waveguide. U.S. Pat. No. 4,443,700 to Macedo shows an optical waveguide which is deformed to change the transmission of different modes in the waveguide.

U.S. Pat. No. 4,399,099 to Buckles shows a fiber-sheath element for quantitative analysis of an analyte species in a fluid with a reactive species. The device has a core which is transmissive to electromagnetic energy, and which is provided with one or more permeable or semipermeable sheaths. Analyte which penetrates the fiber-sheath element reduces or modifies energy transmission by the element in a cumulative manner.

In place of these case by case approaches, it is desired to produce a type of sensor which can be made very small in size, which is highly stable and rugged, which has a wide selection of component materials, which is non-reactive, which has high sensitivity, which provides a simplified measurement methodology, which can be made very specific to any of a wide range of target species, which has a long lifetime, which has selectable thermal properties, which has selectable transmission properties and which is very low cost. The sensor technology should be applicable to detection of a wide variety of chemical species as in process control and monitoring, pollution and environmetal monitoring, and leak detection, and a wide range of biological species as in in vivo and in vitro medical diagnostics, pharmaceutical tests and measurement of drug usage.

Accordingly, it is an object of the invention to provide a general fiber optical chemical sensor design which can be adapted to the measurement of any selected species merely by suitable choice of materials.

It is also an object of the invention to provide a new approach to fiber optic chemical sensor design using the inherent transmission properties of an optical fiber as the basis for detection of a selected species.

It is another object of the invention to provide a custom fiber optic which inherently performs the desired measurement by virtue of its being a fiber optic by proper choice of the materials forming the fiber optic.

It is a further object of the invention to provide a fiber optic chemical sensor which is simple to construct, can be made from an unlimited number of materials, can be made for a wide variety of target species, is extremely easy to operate, and which is very low cost.

SUMMARY OF THE INVENTION

The invention is a new type of chemical sensor which is adaptable to the analysis of several target molecules or classes of compounds. The basic component of the invention is a custom fiber optic which is itself the sensor using the fundamental properties of the fiber as the sensor mechanism. This customized fiber optic is formed by surrounding the fiber core with a clad, or alternatively a reactive layer between the core and an exterior clad, which is made of the sensing material. Thus the fibers are all side coated rather than tip coated. When the target compound specifically interacts with the clad or reactive layer, the optical properties of the clad or reactive layer change, thereby changing the conditions for total internal reflection in the fiber optic sensor and thus affecting light transmission through the fiber. The change in light transmission parameters, particularly intensity and exit angle, caused by the alteration of the clad or reactive layer is measured and directly related to analytical information about the target compound. Absorption reactions can also be used by using a species specific absorber with a nonreactive fluorophore. The same principle is involved in any measurement, with the sensor being made specific to any particular target species by choice of sensor materials.

DETAILED DESCRIPTION OF THE PREFERRED EMBODIMENTS

Figure 1:
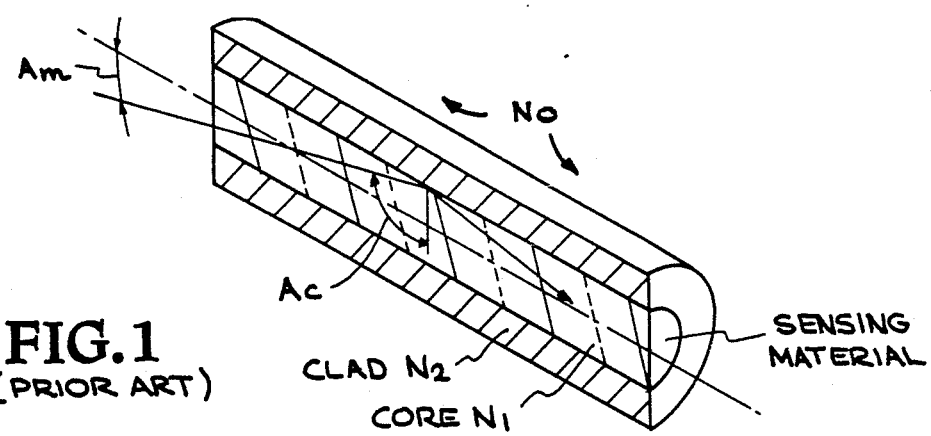
FIG. 1 illustrates a prior art fiber optic chemical sensor.

A typical prior art fiber optical chemical sensor (FOCS) is illustrated in FIG. 1 using a conventional optical fiber for transmitting a light signal from a source to a sensor means at the end of the fiber and back to a detector. The optical fiber transmits light along the core by total internal reflection of the light at the core-clad interface. Light transmission through a fiber optic is an evanescent wave. If the refractive indexes of the core and clad are $N_1$ and $N_2$, respectively, then the critical angle $A_c$, measured from the normal to the surface, at which the light enters the clad is:

$$A_c = \sin^{-1} N_2/N_1$$

For light to propagate through the fiber, it is required that $N_1$ be greater than $N_2$. All light incident at $A_c$ or greater will be totally internally reflected, and thus will propagate along the fiber core. The numerical aperture NA is dependent on the entrance angle of the light $A_m$ through the relationship $$\sin A_m = NA = (N_1^2 - N_2^2)^{\frac{1}{2}}/N_o$$

where $N_o$ is the refractive index of air (or other surrounding medium).

The general approach to fiber optic chemical sensors (FOCS) has been to coat the fiber tip with a reagent that specifically and sensitively interacts with the analyte of interest. Fibers in the 100 to 600 micrometer diameter range are used most often. These have very small surface areas at their tips ($7 \times 10^{-5}$ to $3 \times 10^{-3}$ cm$^2$) and it is difficult to get enough chemistry at the end of the fiber for reliable measurements, i.e., good signal to noise ratio. The sides of the fiber, for all practical purposes, cannot be used because the light does not reach the outer surface of the clad, or in cases where the clad is removed the light comes out the sides and cannot be effectively collected. This lack of surface area has been overcome by a combination of approaches. Fluorescence reactions have been used because of their sensitivity, and surface amplification techniques are employed to increase the amount of reagent that can be attached to the fiber tip. This has led to the use of organic systems, especially fluorphores, which, for many reasons, i.e. lifetime, environmental stability, reproducibility and photodecomposition (bleaching), are not suitable foundations on which to base sensor technology. In special instances this may be the best approach, but only on a limited basis.

Figure 2:
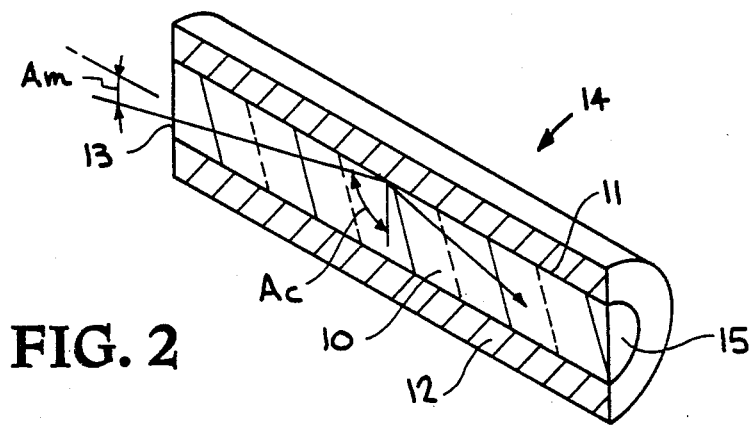
FIG. 2 illustrates a fiber optic sensor with reactive clad in accordance with the invention
Figures 5A, 5B:
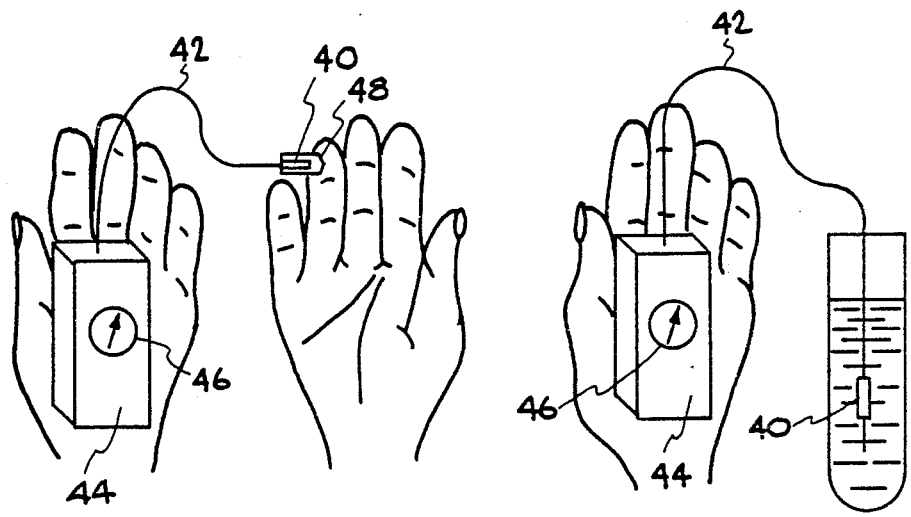
FIGS. 5A and B illustrate two fiber optic diagnostic systems using the sensors of FIGS. 2 and 3.

The invention is a sensor formed of a customized fiber optic which is itself inherently the chemical sensor, i.e. it uses the principles of operation of a fiber optic as the basic detector mechanism. In its most basic embodiment, as shown in FIG. 2, a sensor 14 is formed of a core 10 with a sensing material clad 12. Thus, according to the invention, core 10 transmits a light beam input from a remote source which is preferably connected to one end 13 of sensor 14 by a conventional highly transmissive optical fiber (as shown in FIGS. 5A and B). The core and clad have refractive indexes of $N_1$ and $N_2$, with $N_1$ being greater than $N_2$, so that light incident on the core-clad interface 11 at an angle of $A_c$ (defined as before) or greater will be totally internally reflected and transmitted along the core. The clad is made of a material which is responsive to the chemical species of interest and which changes in the presence of the chemical species to affect the transmission properties of the fiber optic sensor. Thus as $N_2$ changes relative to $N_1$, the angle $A_c$ changes which changes the exit angle $A_m$ (defined as before), or if the change of $N_2$ is sufficiently great (from $N_2$ less than $N_1$ to $N_2$ greater than $N_1$) the sensor may go from transmissive to nontransmissive. This change in transmission properties, e.g. changes in intensity or angle, can be detected, as will be further explained herein, and correlated to a known relationship between the chemical species and clad. The output signal may be transmitted from the other end 15 of sensor 14 to a detector, or end 15 may be reflective and the output signal may be transmitted back to the source.

In accordance with the invention, therefore, the clad which forms the sensing material is chosen first, so that it is possible to: (1) choose the best clad/analyte interaction for the desired measurement, (2) select material(s) that will optimize the clad/analyte interaction, and (3) pick a clad that is stable and will work properly under the prescribed operational conditions.

Once the clad has been chosen then a core must be selected. Criteria for selecting a core material include: (1) choose a core that best "matches" the clad, (2) pick a material that is stable and will work properly under the prescribed operational scenario and (3) select a core that gives optimum light transmission at the desired wavelength.

In this approach the sensor is a custom fiber optic which is attached at the tip of a conventional fiber. It is about 1 to 5 mm long. This very short light path means that the core material for the sensor does not have to follow the normal criteria for good light transmission. In fact, single crystals or powders pressed into rods at high pressure can be used. This gives several advantages: (1) infinite selection of core materials; (2) stability and ruggedness; and (3) selectable refractive index, thermal and light transmission properties.

It is also possible to use the core material as the light source by including a fluorophore or phosphor. This is particularly useful in absorbance type reactions in which the light absorption properties of the clad (or reactive layer) change as a result of interaction with the target molecule. As an example, iodine changes from purple to white so its absorption property changes greatly, and absorption can be measured as well as transmission or angle. By using phosphors or fluorophores as the core material to produce an internal light source, stable light emission properties can be provided to meet the objective of a constant energy source.

The clad can be attached to the core by either vapor deposition, plating or coating, or by any other known technique. This also has several advantages: (1) infinite selection of clad materials (polymers, inorganics, organics, ceramics, polymers with reactant(s) covalently attached to, "trapped" or dissolved in them, etc.); (2) wide selection of reactants, and (3) good choice of physical properties.

The sensor fiber optic is attached to a standard fiber by (1) growing the core single crystal directly on the fiber; (2) placing the standard fiber in a mold and pressing the custom core rod around it; (3) using fiber optic connectors or (4) gluing (with optical cement transparent at the proper wavelength).

Normally in conventional fibers, the evanescent wave does not penetrate very deep into the clad (up to a few monolayers). This is deliberately done so that the light is optimally transmitted through the fiber. In the situation where the clad is the sensing material, however, it is desirable to make a deeper permeation into the clad to provide larger measurable reactive areas. This can be done by properly controlling the wavelength, the angle of the entering light, $N_1$ and $N_2$, as well as the relationship between $N_1$ and $N_2$.

In many instances, however, especially where high sensitivity is required, sensors where clads are only a few monolayers thick are reasonable. Putting down such sparse clads is possible either through controlled vacuum deposition or plating. It should be noted, however, that such systems, by definition have limited lifetimes (very few reactive molecules) except when reversible reactions are possible. The monolayer technology is, for example, suited to the following qualitative and quantitative measurements: (1) water-cobaltous chloride clad goes reversibly blue to pink; (2) cyanide-iodine clad may go reversibly from purple to colorless, and (3) sulfate-barium chloride clad goes irreversibly from clear to white opaque.

Figure 3:
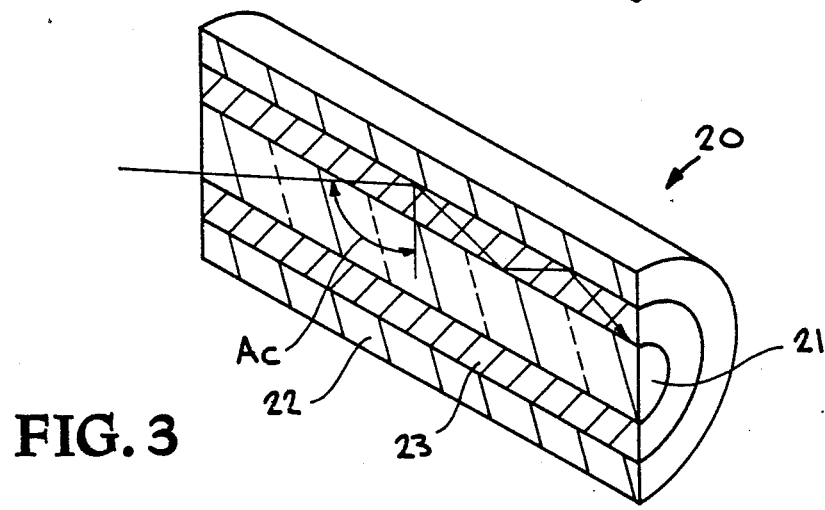
FIG. 3 illustrates a fiber optic sensor with reactive layer between the core and clad in accordance with the invention.

In some cases the clad itself cannot be the sensing material. This may be due to the need for "large" reaction volumes, because the sensing reagents are not suitable for deposition as a clad, or because there are problems with getting the proper $N_2$. This situation is particularly likely where the chemical species to be detected are of biological interest. A multilayered approach where the reacting chemistry is "sandwiched" between the core and the clad as an intermediate reactive layer is illustrated in FIG. 3. A sensor 20 is formed of a core 21 surrounded by a layer of sensing material 23 surrounded by a clad 22. Layer 23 forms an intermediate layer of reactive material on the core and the outer clad forms the fiber optic. The object is to make the refractive index, $N_3$, of the reacting medium greater than $N_1$ and $N_2$ while keeping $N_1$ greater than $N_2$. Thus, because $N_3$ is greater than $N_1$ the light passes through $N_3$ and is sent back to the core when it reaches $N_2$. When it reaches $N_1$ it will also be reflected back through $N_3$ since $N_1$ is less than $N_3$. Thus the reactive layer $N_3$ in effect becomes the fiber optic core, through which light is transmitted, with a fiber optic clad on both the outside and inside surface. The light will make many passes through $N_3$; the indexes should be chosen so that the light passes through the sensor material as many times as possible. Any reactions or interactions that do occur in the reactive layer will change the angle and amount of light that passes through the fiber. Examples of how this may be used to detect and quantify target molecules or classes of compounds include: (1) aromatics-immobilized refractive index-matched polymer sensing volume and a different polymer clad; (2) infectious diseases-monoclonal antibodies immobilized on the core using polymers and a different polymer clad; and (3) biological systems (i.e. CK, bile acids, glucose, etc.)-enzymes immobilized on the core using polymers and a different polymer clad. It should be noted that it is essential that the polymer clad, in addition to having the proper $N_2$, be sufficiently porous so that the species to be monitored have access to the sensor chemistry. The clad can be a membrane to protect the enzyme or monoclonal; the clad may be a polymer with holes of controlled sizes to give a protective and reflective surface. By choosing the porosity and chemical characteristics of the porous clad it can also act as a selective or protective membrane. Anticlotting and/or antifouling agents can be covalently (or electrostatically) attached to the clad. By immobilizing the reactants to the core, any chance of losing the sensing material by "leakage" through the porous polymer clad is obviated. It may also be possible to make multiple sandwiches by layering several sensing materials ($N_3$, $N_4$, etc.) between the core and the clad. Proper selection of $N_1$ and $N_2$ (and $N_3$) make it possible to get a very large change in light transmission for a small concentration of reacting target species.

It is also possible to use absorption reactions by either coimmobilizing a nonreactive fluorophore with a species specific absorber on the fiber core or by using a core made out of a fluorescent or phosphorescent material surrounded by a layer containing the absorber. The fluorophore provides a constant light intensity which increases or decreases as the reversible absorption reactions take place. The measurement of pH can be performed using eosin as the fluorophore and a variety of absorption dyes such as methyl violet (pH 1.5–3.2), congo red (pH 3.0–5.2), litmus (pH 4.5–8.3), phenol red (pH 6.8–8.4), etc. Ammonia, iron and aluminum can also be detected by suitable absorbers, as will be illustrated herein. Chemiluminescence reactions can be used by placing the chemiluminescent reactor in the clad or reactive layer or using it as the clad. Since the light is produced by the chemical reaction itself, an external light source is not needed. As an example, creatine kinase can be detected using luciferase for diagnosis of heart disease.

Figure 4A:
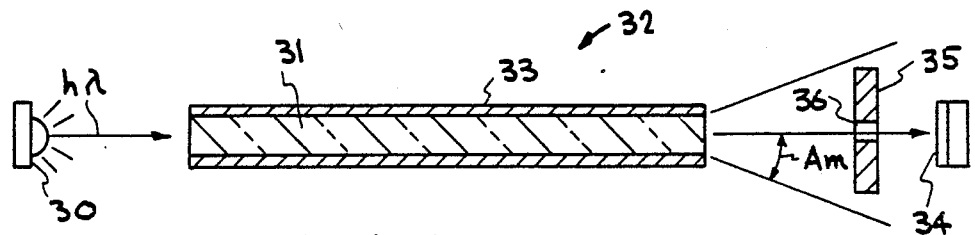
FIGS. 4A and B illustrate two methods of measuring light transmission changes through a fiber optic sensor of the invention.
Figure 4B:
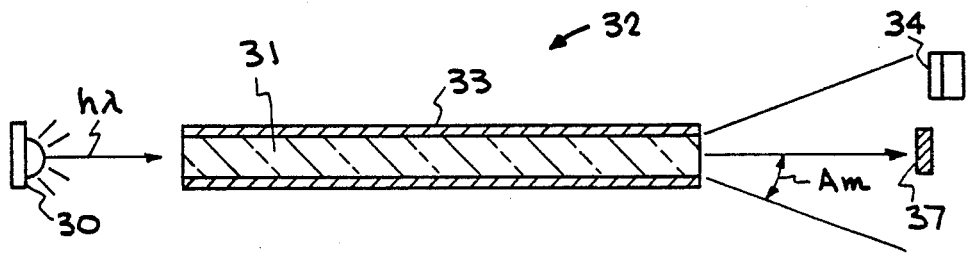

The FOCS are designed so that specificity to a particular molecule or class of compounds is relegated to the sensor chemistry (i.e. choice of materials for the fiber optic) and, therefore, only the amount of light coming out of the fiber and its angle need to be measured. Consequently, it is possible to use a very simple device to make these measurements. As shown in FIGS. 4A and 4B, this would consist of an LED light source 30, the FOCS 32, and a photodiode detector 34. As shown, FOCS 32 has a core 31 and reactive clad 33, of the type shown in FIG. 2, but could alternatively comprise a sensor as shown in FIG. 3 with an intermediate reactive layer in a fiber with a porous clad. Not shown is a small hard wired data collection and processing electronics board, batteries (AA) and an optional miniature recorder (plus batteries). In addition remote sensing can be done by attaching standard fibers to the FOCS to transmit light into the sensor and emitted light back to the detector. It is also possible to put the detector with the FOCS and transmit an electrical signal back to the output device. In FIG. 4A the detector is shown on axis so it sees more of the emitted light and has maximum sensitivity to changes in light output. A beam stop 35 with central hole 36 is positioned between the FOCS and detector to pass on-axis light and block off-axis light. The arrangement shown in FIG. 4B uses an off axis detector and sees less light but is more sensitive to changes in the output angle of the light. An on-axis beam stop 37 blocks the on-axis light. Thus the set up shown in FIG. 4B is exceptionally useful when changes in $A_c$ are key to the measurement.

Illustrative embodiments of a complete, compact, hand-held sensor system are shown in FIGS. 5A and B for in vivo and in vitro applications, respectively. A sensor 40 of the type shown in FIGS. 2 and 3 and made of materials chosen for the specific target species of interest, is connected to one end of a standard transmitting fiber optic 42 which is connected at the other end to a monitor unit 44 which contains the illumination source as well as the detection means and data processing means. Monitor unit 44 has a simplified read out 46. For in vivo diagnostic measurements sensor 40 may be contained within a stick/needle 48 to facilitate insertion into the body while in the in vitro or standard chemical measurement case the sensor is merely placed in the sample or environment. Any configuration of light source (e.g. laser), detector and signal processing could be used with the fiber optic sensor of the invention as would be apparent to one skilled in the art.

Therefore, this new approach to FOCS has many benefits. Some of the key ones include: (1) a single technology on which many FOCS can be based; (2) the use of chemicals and components which are inherently stable, long-lived and safe; (3) FOCS which are amenable to bulk manufacture at low cost (manufacturing cost less than $5 per sensor); and (4) readers which are simple, inexpensive and easy to manufacture (manufacturing cost less than $350 per unit). The sensitivity of the basic sensor is in the sub-ppm range, while the sandwich embodiment can be tailored to operate from the sub-ppm to the percent range because it can be made to contain controlled amounts of reactive layer and selected excitation path lengths.

EXAMPLE I

To detect water, a fiber optic sensor is formed of a cobaltous chloride clad on a suitable core (of greater refractive index). Water causes cobaltous chloride to change reversibly blue to pink. Thus blue light is transmitted through the sensor core. In the absence of water, the blue light is totally internally reflected by the clad (blue). In the presence of water, the clad turns pink (which absorbs blue light) so the blue light signal is decreased. The measurement may either be qualitative or quantitative. Multiple wavelength sources may be used to enhance sensitivity.

EXAMPLE II

To detect cyanide, a fiber optic sensor is formed of an iodine clad on a suitable core (of greater refractive index). Cyanide causes iodine to change reversibly purple to colorless. Thus purple light is transmitted through the sensor core. In the absence of cyanide, the purple light is totally internally reflected by the clad (purple). In the presence of cyanide, the clad turns colorless (which absorbs all light) so the purple light signal is decreased. The measurement may either be qualitative or quantitative.

EXAMPLE III

To detect sulfate, a fiber optic sensor is formed of a barium chloride clad on a suitable core (of greater refractive index). Sulfate causes barium chloride to change reversibly clear to white opaque. Thus white light is transmitted through the sensor core. In the absence of sulfate, the white light is totally internally reflected by the clad (clear). In the presence of sulfate, the clad turns white opaque (which scatters all light) so the white light signal is decreased. The measurement may either be qualitative or quantitative.

EXAMPLE IV

To detect bile acids, a fiber optic sensor is formed of the enzyme $3\alpha$-hydroxysteroid dehydrogenase and the co-enzyme NAD coimmobilized on a glass core through the use of a polymer whose refractive index is greater than the core. A porous polymer clad, typically with 0.2 micron pore size, is attached to the enzyme and also acts as a protective membrane. When bile acids react with the enzyme a hydrogen is released which converts nonfluorescent NAD to fluorescent NADH. Excitation is at 340 nm and detection at 480 nm. The $7\alpha$, $12\alpha$, etc. enzymes can also be used to increase specificity for single bile acid identification and quantification. A second identical fiber, without the enzyme or coenzyme is used to monitor naturally present NADH so it can be subtracted from the bile acid reading.

This general approach is applicable to the use of many single or mixed enzyme systems. One or more enzymes can be covalently bonded in a single reactive layer or in multiple reactive layers. An alcohol sensor could be based on an alcohol enzyme (e.g. alcohol dehydrogenase) and a glucose sensor on the glucose enzyme glucose oxidase.

EXAMPLE V

To detect (infectious) diseases, a fiber optic sensor is formed using species specific monoclonal antibodies immobilized on a glass core through the use of a polymer whose refractive index is greater than the core. A porous polymer clad is attached to the monoclonal antibody and also acts as a protective membrane. When the antigen (disease) reacts with the monoclonal antibody, its refractive index changes, thus changing the amount and angle of white light transmitted through the fiber. The monoclonal is ultraspecific to the target species, thus making identification unambiguous while light intensity and angle can be related to the quantitative information being sought.

It is also possible to attach a fluorescent tag such as eosin to the antibody which is ejected when the antigen reacts. The eosin is excited to fluorescence at 475 nm and emits at 552 nm. Decrease of fluorescence due to fluorophore ejection is a good quantitative measurement. Thus the change in intensity or angle at 475 nm as well as the change in intensity at 552 nm can be measured.

This general approach, untagged or tagged with a fluorescent compound, is suitable for direct assays for all compounds for which specific monoclonals exist. It is also applicable to polyclonal antibodies.

EXAMPLE VI

To detect organic compounds of a particular class, group, or individually, a clad is formed using a material, usually a polymer or silyl compound whose refractive index is matched to the target material over its concentration range in the background matrix of interest, e.g. gasoline 1-100 ppm in air or gasoline 0.1-10 ppm in water. In this case a core material is then chosen whose refractive index is greater than the largest refractive index provided for. As the target molecule interacts with the clad it changes its refractive index thus reducing and/or increasing light transmission and the exit angle of the light. The refractive index match is used to identify the species being measured and light intensity and angle is used for quantification. The proper selection of clad refractive index can also be used to provide an "off/on" switch for when a species concentration has been exceeded. This technique has particular application in measuring organic compounds and mixtures of organic compounds in air and water. Particular compounds or materials which can be detected by this approach are gasoline, kerosene, jet fuel (JP4), aliphatic and aromatic hydrocarbons.

EXAMPLE VII

Ammonia can be detected using the reagent indophenol. Indophenol and a fluorophore such as eosin are coimmobilized either as the clad or the reactive layer. The eosin is excited by a laser source at 475 nm and emits its own fluorescence at 552 nm. Eosin is chosen because it is pH independent and is an effective stable light source. As the ammonia reacts with the indophenol, indophenol blue is formed which absorbs the eosin emission. Reduction in the fluorescence signal can be related to the amount of ammonia coming into contact with the indophenol, thus providing quantitative information.

Similarly, iron can be detected using 1,10 phenanthroline; a red color is formed which is more absorbing to the eosin emission. Aluminum can be detected using pyrocatechol which is initially violet and a strong absorber. As the reaction occurs, the violet fades with a decrease in absorption of the eosin emission and an increase in the transmitted signal.

The detection and quantification of biological agents or diseases is based on the use of monoclonal antibodies as the sensing material. Either configuration, monoclonals in the clad and monoclonals sandwiched between the core and clad, may be used. There are numerous monoclonal antibodies commercially available which cover the range for such target molecules (antigenic specific) as pollutants, infectious agents, chemical agents, drugs, cancer diagnostic and therapeutic compounds, and other materials of medical and toxilogical interest; other special monoclonals can be made for sensor use. In accordance with the invention the sensor design and chemistry are fixed; the only variable is the monoclonal antibody. However it may be necessary to adjust the way the antibody is attached to the fiber to accomodate differences in monoclonal structures. Because of the high specificity of monoclonal antibodies, a different sensor will be needed for each agent or disease. But if specificity can be traded for fewer sensors, then polyclonals, enzymes, etc. can be used.

In either embodiment the antibodies are covalently bonded to the core material to assure chemical stability; glass fibers are preferred. Monoclonals can also be immobilized on other surfaces using other intermediary chemicals. The approach to coupling antibodies (and enzymes) to glass fibers is to synthesize branched polyethylene oxides (PEOs) with activation sites for attaching monoclonal antibodies. PEOs have several desirable properties including: solubility in water and organic solvents, ease of synthesis and attachment to other molecules, and increased biological stability of PEO-antibody conjugates. This assures retention of the reactivity and specificity of the monoclonal antibodies.

A preferred polymer is the branched PEO made by including some glycidol anion in the ethylene oxide polymerization.

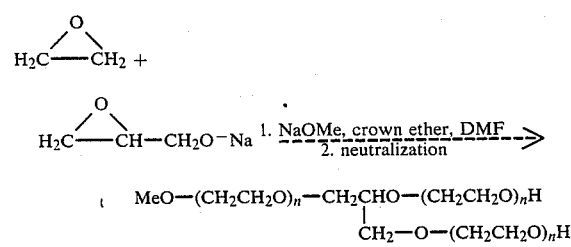

This synthesis is effective for preparing polymers of Mw up to 3000 g/mol. As described below, the hydroxyl-terminated polymer can then be activated toward nucleophilic attack (step 1), attached to amino groups on the glass surface (step 2), and then coupled with amino groups on the monoclonal antibodies.

The primary polymer is modified by inclusion of three copolymers. First, the diethyl acetal of glycidal is included in the polymerization. This polymer has (after hydrolysis of the acetal) aldehyde groups along the chain, thus providing the opportunity for reductive amination with amines (such as monoclonal protein lysines and amino-glass). Second, butadiene epoxide is included to introduce crosslinking. Third, propylene oxide is included for hydrophobicity (inclusion of approximately 75% propylene oxide gives a water-insoluble polymer).

Two variations in the polymerization process can also be used. In addition to methoxide as initiator, polymerization can be initiated directly by amino groups on the glass surface. The benefit of direct polymerization on the surface is that the branched polymer is attached only at one point, thus making more sites available for attaching the monoclonal antibodies. The other route of attaching activated polymer to the amino-functionalized surface gives multiple attachment at sites which could also serve for attaching monoclonal antibody. Additionally, initiation by Vandenberg-type aluminum alkoxide catalysts can be used; these catalysts are well characterized and quite versatile, and may give more control than provided by crown-base initiation.

The first step in coupling polymers to glass and monoclonal antibodies is to activate the polymer toward nucleophilic attack by amines. Activated derivatives used include the cyanuric-chloride derivative, the carbonyl diimidazole derivative, the tresylate, and the succinimidyl succinate. All give active monoclonal antibody conjugates; the tresylate is preferred as it gives coupling through a relatively stable amine linkage. Polymer prepared by direct polymerization on amino-glass can then be activated on the glass.

Activated polymers can be coupled to glass which has had amine groups covalently bonded to its surface. This amino-glass can be prepared either by reacting with trialkoxylaminopropylsilane or with ammonia in a plasma discharge. Polymer can also be grown directly on the amino-glass.

Two specific approaches can be taken in the immobilization/surface amplification preparation of proteinaceous sensing materials (PSM) including monoclonal antibodies, polyclonal antibodies, and enzymes. In both syntheses the starting point is the polymerization of the PEO to a branched polyethylene glycol, B-PEG:

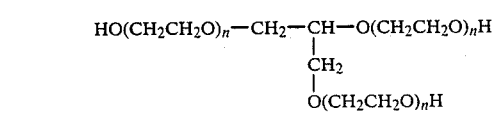

The degree of branching is controlled by the amount of

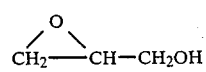

included in the polymerization of

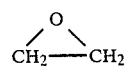

The B-PEG is electrophilically activated as follows:

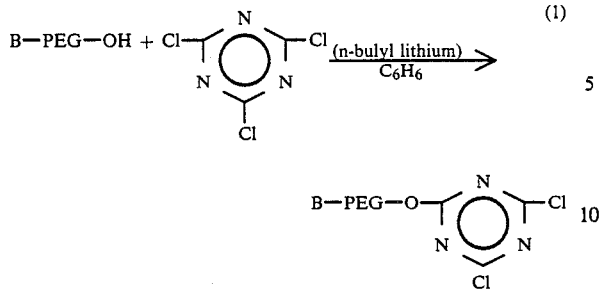

(1)

(2)

It is then reacted with the PSM where the —NH$_2$ on the PSM is from the lysine subunits. An excess of the electrophilically activated B-PEG is used so that there are sites available to attach the B-PEG-PSM to the fiber optic.

The silica fiber optic is nucleophilically activated using a silyl compound:

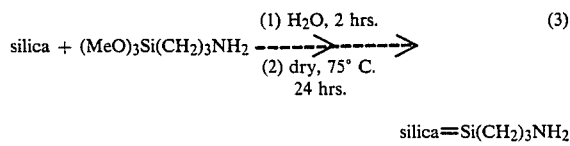

(3)

silica═Si(CH$_2$)$_3$NH$_2$

The B-PEG-PSM is then attached as follows:

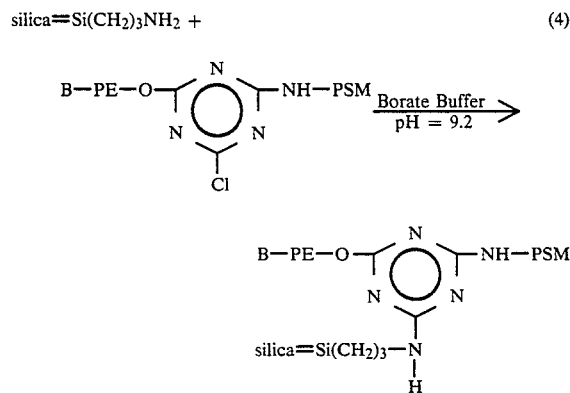

(4)

A second approach is to attach amino-branched PEG

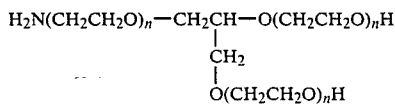

to an electrophilically activated fiber optic made from the silyl prepared silica (Eq. 3):

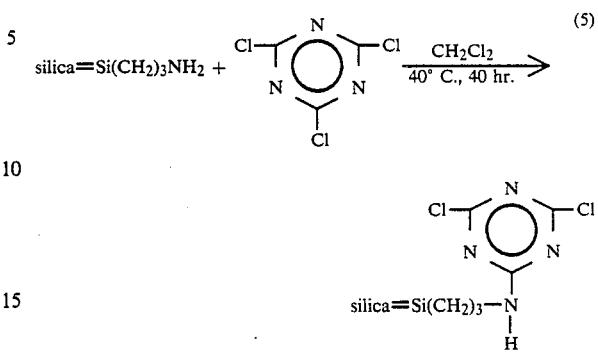

(5)

This has the advantage of attaching the branched polymer to the silica by a single covalent bond. The surface bound polymer can then be activated as shown in Eq. 1 and the enzyme bound to the activated polymer as shown in Eq. 2.

Attaching the monoclonal antibody (MA) to the glass is a key part of forming the sensor. When the MA/B-PEG is the clad, the refractive index of the core has to be greater than that of the MA/B-PEG. When the MA/B-PEG is in a sandwich between the core and the clad, the refractive index of the core must be less than the MA/B-PEG and that of the clad less than the core.

Coupling of monoclonal antibodies to activated, glass bound polymer is straightforward since the monoclonal antibody has an appreciable number of subunits which terminate in —NH$_2$. Additionally monoclonal antibody lysine subunits can be coupled to the glycidal-containing polymer by reductive amination with sodium cyanoborohydride.

Direct measurement of the antigen-monoclonal antibody reaction should be sufficiently sensitive for required diagnoses. If, however, additional sensitivity is required, fluorescent tags can be used. Changes in fluorescence intensity, spectral shifts, etc. which result from antibody interaction may be measured. Tags are attached in a similar manner to the monoclonals. A fluorophore such as eosin is preferred because it has good quantum efficiency and is pH insensitive in the physiological range. The eosin can either be attached to the monoclonal or it can be coimmobilized with the monoclonal using the PEO. Amine derivatives for reaction with the activated polymer can be prepared by standard procedures, e.g. reduction of isocyanate (e.g. eosin isocyante) with lithium aluminum hydride.

Changes and modifications in the specifically described embodiments can be carried out without departing from the scope of the invention which is intended to be limited only by the scope of the appended claims.

I claim:

1. A method of forming a chemically or biologically sensing optical fiber having a core which transmits light of a predetermined wavelength and a fiber optic clad surrounding the core and made of a material with an index of refraction less than the core and which reacts with a predetermined chemical or biological species to produce measurable changes in the transmission of light through the optical fiber in the presence of the predetermined chemical or biological species, the method comprising:

first selecting a clad material for its reaction properties with the predetermined chemical or biological species;

then selecting a core material which is effectively index matched to the clad to form an optical fiber;

forming a fiber optic element from the thus-selected core and clad materials.

2. The method of claim 1 wherein the core is formed of a single crystal.

3. The method of claim 1 wherein the core is formed of a pressed powder rod.

4. The method of claim 1 wherein the sensing optical fiber is formed of a length of about 1-5 mm.

5. A chemically or biologically sensing optical fiber formed by the method of claim 1.

6. The chemically or biologically sensing optical fiber of claim 5 further comprising:

a light source of the predetermined wavelength operatively coupled to the sensing optical fiber;

detection means operatively coupled to the sensing optical fiber for detecting changes of transmission of light from the light source through the optical fiber.

7. The sensor of claim 6 wherein the light source is operatively coupled to the sensing optical fiber by a transmitting optical fiber.

8. The sensor of claim 6 wherein the clad is selected from the group consisting of cobaltous chloride, iodine, and barium chloride.

9. The sensor of claim 6 for detecting a target organic compound, including gasoline, kerosene, jet fuel, aliphatic and aromatic hydrocarbons, wherein the clad is formed of a material whose refractive index is matched to the target compound over a predetermined concentration range, and the core is formed of a material with a refractive index greater than the largest refractive index of the clad.

10. The sensor of claim 6 for detecting a predetermined antigen wherein the clad comprises a polymer with attached monoclonal antibodies specific to the predetermined antigen.

11. The sensor of claim 6 wherein the element further includes an internal light source selected from the group consisting of phosphors and fluorophores.

12. The sensor of claim 11 wherein the clad further includes an absorber material which is reactive with the predetermined chemical or biological species to modify its absorption of light produced by the phosphors and fluorophores.

13. The optical fiber of claim 5 for detecting a target organic compound, including gasoline, kerosene, jet fuel, aliphatic and aromatic hydrocarbons, wherein the clad is formed of a material whose refractive index is matched to the target compound over a predetermined concentration range, and the core is formed of a material with a refractive index greater than the largest refractive index of the clad.

14. The optical fiber of claim 5 wherein the clad includes a proteinaceous sensing material selected from the group consisting of monoclonal antibodies, polyclonal antibodies, and enzymes.

15. The optical fiber of claim 5 for detecting a predetermined antigen wherein the clad comprises a polymer with attached monoclonal antibodies specific to the predetermined antigen.

16. The optical fiber of claim 5 wherein the clad comprises a first polymer with attached enzymes.

17. The optical fiber of claim 16 wherein the enzyme is selected from the group consisting of 3α-hydroxysteroid hydrogenase with NAD, alcohol dehydrogenase, and glucose oxidase.

18. A chemically or biologically sensing optical fiber comprising:

a core which transmits light of a predetermined wavelength;

a reactive layer surrounding the core and made of a material which reacts with a predetermined chemical or biological species to produce measurable changes in the transmission of light through the optical fiber in the presence of the predetermined chemical or biological species;

a fiber optic clad surrounding the reactive layer and which is porous to the predetermined chemical or biological species;

wherein the reactive layer has an index of refraction greater than the core and the core has an index of refraction greater than the clad.

19. The optical fiber of claim 18 for a predetermined antigen wherein the reactive layer comprises a polymer with attached monoclonal antibodies specific to the predetermined antigen and the clad comprises a second polymer.

20. The chemically or biologically sensing optical fiber of claim 18 further comprising:

a light source of the predetermined wavelength operatively coupled to the sensing optical fiber;

detection means operatively coupled to the sensing optical fiber for detecting changes of transmission of light from the light source through the optical fiber.

21. The sensor of claim 20 for a predetermined antigen wherein the reaction layer comprises a polymer with attached monoclonal antibodies specific to the predetermined antigen and the clad comprises a second polymer.

22. The sensor of claim 20 wherein the reactive layer comprises a first polymer with attached enzymes and the clad comprises a second polymer.

23. A chemically or biologically sensing optical fiber comprising:

a core which transmits light of a predetermined wavelength;

a fiber optic clad surrounding the core and made of a material with an index of refraction less than the core and which reacts with a predetermined chemical or biological species to produce measurable changes in transmission of light through the optical fiber in the presence of the predetermined chemical or biological species;

an internal light source selected from the group consisting of phosphors and fluorophores.

24. The optical fiber of claim 23 wherein the clad further includes an absorber material which is reactive with the predetermined chemical or biological species to modify its absorption of light produced by the phosphors and fluorophores.

25. The optical fiber of claim 24 wherein the fluorophore is eosin and the absorber is selected from the group consisting of indophenol, 1,10 phenanthroline, and pyrocatechol.

26. A method of detecting the presence of a predetermined chemical or biological species comprising:

forming a chemically or biologically sensing optical fiber having a core which transmits light of a predetermined wavelength and a fiber optic clad surrounding the core and made of a material with an index of refraction less than the core and which reacts with a predetermined chemical or biological species to produce measurable changes in the transmission of light through the optical fiber in the presence of the predetermined chemical or biological species by the steps of first selecting a clad material for its reaction properties with the predetermined chemical or biological species, (b) then selecting a core material which is effectively index matched to the clad to form an optical fiber, (c) forming a fiber optic element from the thus-selected core and clad materials;

transmitting a light beam of the predetermined wavelength into the sensing optical fiber;

detecting changes in the transmission of the light beam through the sensing optical fiber caused by reaction of the clad with the predetermined chemical or biological species.

27. The method of claim 26 wherein the step of detecting changes in the transmission of the fiber is performed by measuring changes in intensity of the light beam.

28. The method of claim 26 wherein the step of detecting changes in the transmission of the fiber is performed by measuring changes in the exit angle of the light beam from the fiber.

29. The method of claim 26 further including providing a fluorophore in the element which is excited by the light of the predetermined wavelength and emits light of a second wavelength, and providing an absorber material in the first clad which is reactive with the predetermined chemical or biological species to modify its absorption of light of the second wavelength.

30. The method of claim 29 further including measuring changes in intensity of light of the second wavelength.

31. The method of claim 26 further including forming the clad of a proteinaceous sensing material (PSM) selected from the group consisting of monoclonal antibodies, polyclonal antibodies, and enzymes.

32. The method of claim 31 further including:
forming branched polyethylene glycol (PEG);
activating the surface of the branched PEG to provide sites for attaching the PSM;
reacting the activated PEG with the PSM.

33. A chemically sensing optical fiber comprising:
a clad selected from the group consisting of cobaltous chloride, iodine, and barium chloride;
a core having a refractive index greater than the clad and selected to effectively match the clad.

34. A method of detecting the presence of a predetermined chemical or biological species comprising:
forming a chemically or biologically sensing optical fiber having a core which transmits light of a predetermined wavelength, a reactive layer surrounding the core and made of a material which reacts with a predetermined chemical or biological species to produce measurable changes in the transmission of light through the optical fiber in the presence of the predetermined chemical or biological species, and a fiber optic clad surrounding the reactive layer and which is porous to the predetermined chemical or biological species, wherein the reactive layer has an index of refraction greater than the core and the core has an index of refraction greater than the clad;

transmitting a light beam of the predetermined wavelength into the sensing optical fiber;

detecting changes in the transmission of the light beam through the sensing optical fiber caused by reaction of the clad with the predetermined chemical or biological species.

* * * * *